US006331180B1

(12) United States Patent
Cosman et al.

(10) Patent No.: US 6,331,180 B1
(45) Date of Patent: *Dec. 18, 2001

(54) TARGET-CENTERED STEREOTAXTIC SURGICAL ARC SYSTEM WITH REORIENTATABLE ARC AXIS

(75) Inventors: Eric R. Cosman, Belmont, MA (US); Trent H. Wells, Jr., Coulterville, CA (US)

(73) Assignee: Sherwood Services AG, Schaffhausen (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/909,655

(22) Filed: Aug. 12, 1997

Related U.S. Application Data

(63) Continuation of application No. 08/632,596, filed on Apr. 15, 1996, now abandoned, which is a continuation of application No. 08/472,732, filed on Jun. 7, 1995, now abandoned, which is a continuation of application No. 08/207,793, filed on Mar. 7, 1994, now abandoned, which is a continuation of application No. 07/921,955, filed on Jul. 29, 1992, now abandoned, which is a continuation of application No. 07/764,108, filed on Sep. 23, 1991, now abandoned, which is a continuation of application No. 07/631,227, filed on Dec. 21, 1990, now abandoned, which is a continuation of application No. 07/478,757, filed on Feb. 12, 1990, now abandoned, which is a continuation of application No. 07/189,568, filed on May 3, 1988, now abandoned.

(51) Int. Cl.⁷ .................................................. A61B 19/00
(52) U.S. Cl. .............................................................. 606/130
(58) Field of Search .................................... 606/130, 129; 600/417

(56) References Cited
U.S. PATENT DOCUMENTS

| 2,697,433 | * | 12/1954 | Zehnder | 128/303.1 X |
| 3,135,263 | * | 6/1964 | Connelley | 128/303 B |
| 3,777,124 | | 12/1973 | Pavkovich | |
| 4,222,104 | | 9/1980 | Moore | |

(List continued on next page.)

FOREIGN PATENT DOCUMENTS

| 2139433 | * | 2/1973 | (DE) | 128/303 B |
| 0018166 | | 10/1980 | (EP) | |
| 2094590 | | 9/1982 | (GB) | |
| 2213066 | | 8/1989 | (GB) | |
| 764670 | * | 9/1980 | (SU) | 128/303 B |
| WO 9428817 | | 12/1994 | (WO) | |
| WO 9637158 | | 11/1996 | (WO) | |
| WO 9740766 | | 11/1997 | (WO) | |

OTHER PUBLICATIONS

"Tumor Stereotaxis", Patrick J. Kelly, M.D., W.B. Saunders Company (1991).

Primary Examiner—Michael H. Thaler

(57) ABSTRACT

Stereotaxic Arc Systems are common instruments in neurosurgery for accurately directing a probe into the head and brain. Among the many types of arc concepts for such instruments is the target-centered arc. This involves an arc system which provides spherical radii from a multiplicity of directions depending on the rotation angles of the arc. All of the radii converge to the target point, thus the name target-centered arc. Prior to this invention, all such systems with two trunion bearings have an axis of arc rotation which has a fixed orientation relative to the patient's head. This causes a limitation in directions of approaches to desired targets. The present invention involves a new concept of target-centered arc, in which the access of rotation of the two trunions and their connected arc itself can be varied in orientation, leading to an unprecedented wide range of approaches to any anatomical target and great versatility of the arc system in surgery.

3 Claims, 2 Drawing Sheets

U.S. PATENT DOCUMENTS

| | | |
|---|---|---|
| 4,262,306 | 4/1981 | Renner . |
| 4,341,220 | 7/1982 | Perry . |
| 4,350,159 * | 9/1982 | Gouda .............................. 128/303 B |
| 4,463,758 | 8/1984 | Patil et al. . |
| 4,583,538 | 4/1986 | Onik et al. . |
| 4,592,352 | 6/1986 | Patil . |
| 4,608,977 * | 9/1986 | Brown .............................. 128/303 B |
| 4,617,925 | 10/1986 | Laitinen . |
| 4,618,978 | 10/1986 | Cosman . |
| 4,638,798 | 1/1987 | Shelden et al. . |
| 4,651,335 | 3/1987 | Kalender et al. . |
| 4,706,665 | 11/1987 | Gouda . |
| 4,791,934 | 12/1988 | Brunnett . |
| 4,838,265 | 6/1989 | Cosman et al. . |
| 4,841,967 | 6/1989 | Chang et al. . |
| 4,869,247 | 9/1989 | Howard, III et al. . |
| 4,896,673 | 1/1990 | Rose et al. . |
| 4,955,891 | 9/1990 | Carol . |
| 5,027,818 | 7/1991 | Bova et al. . |
| 5,047,036 | 9/1991 | Koutrovelis . |
| 5,050,608 | 9/1991 | Watanabe et al. . |
| 5,056,523 | 10/1991 | Hotchkiss, Jr. et al. . |
| 5,078,140 | 1/1992 | Kwoh . |
| 5,080,662 | 1/1992 | Paul . |
| 5,107,839 | 4/1992 | Houdek et al. . |
| 5,117,829 | 6/1992 | Miller et al. . |
| 5,129,911 | 7/1992 | Siczek et al. . |
| 5,142,559 | 8/1992 | Wielopolski et al. . |
| 5,163,430 | 11/1992 | Carol . |
| 5,165,410 | 11/1992 | Warne et al. . |
| 5,178,146 | 1/1993 | Giese . |
| 5,186,174 | 2/1993 | Schlondorff et al. . |
| 5,197,476 | 3/1993 | Nowacki et al. . |
| 5,207,223 | 5/1993 | Adler . |
| 5,211,164 | 5/1993 | Allen . |
| 5,221,283 | 6/1993 | Chang . |
| 5,230,623 | 7/1993 | Guthrie et al. . |
| 5,242,455 | 9/1993 | Skeens et al. . |
| 5,247,555 | 9/1993 | Moore et al. . |
| 5,257,998 | 11/1993 | Ota et al. . |
| 5,269,305 | 12/1993 | Corol . |
| 5,281,232 | 1/1994 | Hamilton et al. . |
| 5,285,772 | 2/1994 | Rattner . |
| 5,285,787 | 2/1994 | Machida . |
| 5,295,483 | 3/1994 | Nowacki et al. . |
| 5,299,254 | 3/1994 | Dancer et al. . |
| 5,300,080 | 4/1994 | Clayman et al. . |
| 5,309,913 | 5/1994 | Kormos et al. . |
| 5,315,630 | 5/1994 | Sturm et al. . |
| 5,329,567 | 7/1994 | Ikebe . |
| 5,354,314 | 10/1994 | Hardy et al. . |
| 5,383,454 | 1/1995 | Bucholz . |
| 5,387,220 | 2/1995 | Pisharodi . |
| 5,389,101 | 2/1995 | Heilbrun et al. . |
| 5,398,684 | 3/1995 | Hardy . |
| 5,423,832 | 6/1995 | Gildenberg . |
| 5,446,548 | 8/1995 | Gerig et al. . |
| 5,464,411 | 11/1995 | Schulte et al. . |
| 5,588,430 | 12/1996 | Bova et al. . |
| 5,622,170 | 4/1997 | Schulz . |
| 5,662,111 | 9/1997 | Cosman . |
| 5,682,890 | 11/1997 | Kormos et al. . |
| 5,715,836 | 2/1998 | Kliegis et al. . |
| 5,769,861 | 6/1998 | Vilsmeier . |
| 5,776,064 | 7/1998 | Kalfas et al. . |
| 5,792,146 | 8/1998 | Cosman . |
| 5,792,147 | 8/1998 | Evans et al. . |
| 5,836,954 | 11/1998 | Heilbrun et al. . |
| 5,848,967 | 12/1998 | Cosman . |
| 5,961,454 | 10/1999 | Kooy et al. . |
| 5,971,997 | 10/1999 | Guthrie et al. . |
| 6,006,126 | 12/1999 | Cosman . |

* cited by examiner

TARGET-CENTERED STEREOTAXTIC SURGICAL ARC SYSTEM WITH REORIENTATABLE ARC AXIS

This application is a continuation of application(s) Ser. No. 08/632,596 filed on Apr. 15, 1996 now abandoned, which is a continuation Ser. No. 08/472,732 filed Jun. 7, 1995, now abandoned, which is a continuation of Ser. No. 08/207,793 filed Mar. 7, 1994, now abandoned, which is a continuation of Ser. No. 07/921,955 filed Jul. 29, 1992, now abandoned, which is a continuation of Ser. No. 07/764,108 filed Sep. 23, 1991, now abandoned, which is a continuation of Ser. No. 07/631,227 filed Dec. 21, 1990, now abandoned, which is a continuation of Ser. No. 07/478,757 filed Feb. 12, 1990, now abandoned, which is a continuation of Ser. No. 07/189,568 filed May 3, 1988 now abandoned.

BACKGROUND TO THE INVENTION

A stereotaxic arc system is a device commonly used in neurosurgery to quantitatively and accurately direct a probe into the body to a desired target seen on x-rays or tomographic imaging. There have been dozens of such devices invented in the last forty years. One class of such stereotaxic systems is the so-called target-centered arc concept. In this concept, an arc system which has been coupled by various means to the patient's body, as in the case of neurosurgery by fixation means to the skull, and the arc elements themselves can be rotated so as to provide radio guidance direction for a probe into the head. FIG. 1 illustrates the prior art in target-centered stereotaxic systems. Typically, the major arc element 1 is a so-called transverse arc which is usually a segment of a circular arc that rotates on a bearing or bearings 5a and 5b at one end, sometimes referred to as trunions. It further has a slide element 2 that runs along it which carries the probe guide 2a. With a combination of the rotation of the arc 1 about its axis and the probe slide 2 on the arc, one can achieve an infinite number of spherical radii 3 to the center 4 of the circular arc. The anatomical target, furthermore, is placed at the center of these arc radii, thereby enabling that all radii 3 will pass through that target 4. To move the target to the center of the arc, usually one has means to translate the arc in Cartesian or rectilinear movements, x, y and z, or in clinical jargon, anterior-posterior (A-P), lateral, and vertical. Typically, this is done by either moving the patient's head itself so that the target is at the center of the arc, or by moving the arc relative to the patient, who is secured in a head ring, to achieve the same end. Thus, the name target-centered arc means that the target is placed at the center of a spherical arc system. This construction has great utility'since once the target has been identified, that is its A-P, lateral, and vertical coordinates determined by x-ray or tomographic scanning, the target can be moved quantitatively by means of Cartesian slides so that the target lies at the center of the arc system. Thus, the surgeon may have great flexibility in choosing the desired arc settings for an optimal approach to the target.

There are many popular arc systems on the market today and designed over the past forty years which use this concept. Among them are the Todd-Wells Guide (USA), the Leksell System (Sweden), the Hitchcock (UK), the Laitinen System, and the Patil System (USA). All of these systems have the same basic characteristics. They have an arc system, which we can refer to as a transverse arc, which rotates about an axis relative to a base structure or base frame. The structure itself is coupled to the patient's head, and the head can be translated in Cartesian coordinates, x, y and z, or equivalently, A-P, lateral, and vertical, so that the anatomical target can be moved to what is the center of the radii that are defined by the circular arc. The circular transverse arc 1 can be moved on a bearing or trunion 5a or 5b about the axis of rotation 7. In addition, a probe guide carrier or transverse slide 2 moves along the circular arc to give a second angular degree of freedom. The combination of the arc rotation on its trunion or axis and the transverse slide movement can enable any probe direction 3 to be achieved. Since the target is at the isocenter of the two arc movements, that is all radii constitute radii for a sphere converging to the point 4 where the target 4 is located, then the probe automatically, when directed radially, will achieve the target from any of the slide or arc movement directions. This is the arc-centered or target-centered concept.

Although this target-centered design is simple and easy-to-use, in the two trunion designs prior to this invention there have been limitations in the angular range that the probe guide can achieve the target. In particular, the bearing or trunion 5a or 5b is always fixed in a particular location relative to the base frame 271 and thus relative to the patient's head, or to a body-fixed coordinate axis such as the anterior direction 6 as shown in FIG. 1. For example, in the Todd-Wells and Leksell, Patil, and Laitinen frames, the trunions are always located laterally or to the side of the patient's head (axis labeled by R (right) and L (left in FIG. 1), and thus at a fixed angular orientation relative to the target which is the center of the arc. This means that since the slide 2 cannot come down and pass the trunion position of 5a and 5b (or the bearing, if that is what supports the arc 1), then there is always a blind spot in the range of motion of the slide, where the probe cannot pass because it is obstructed by the trunion. Also, if you want a pure lateral approach, that is to say, an approach where the probe goes through the trunion hole, for example, you have limitations in the clearance between the probe and the trunion hole, which is restrictive in a surgical context. Typically too, these instruments have other structural obstructions to probe movement. For example, in the Leksell and Patil the transverse arc at certain angular orientations and slide positions will present an obstruction of the probe path by hitting the frame structure that supports the transverse arc and trunions itself.

The Hitchcock frame has only one trunion and only a partial arc segment for its transverse arc. This means it has a limited transverse arc range for a given trunion position and has less stability than the two trunion design show in FIG. 1. It does have a reorientable single trunion axis, but the limitations of the of the single trunion restrict its range and usefulness.

An objective of the present invention is to circumvent these limitations to the target-centered arc concept. The essential means by which we have done this in the present invention is to provide a way that the two trunions 5a and 5b themselves, and thus the axis of orientation 7 of their transverse arc, can be changed relative to the base frame 271 or the body-fixed coordinate axes such as 6 (anterior). For example, the trunions, instead of being placed laterally left and right on the patient's head, can be changed to an A-P, or anterior-posterior, orientation without having to release the patient's head from the frame and put the frame on at 90°. This concept of a movable two trunion angular orientation relative to the patient's head has been described in a paper by Cosman and Wells presented at the Stereotaxic Society Meeting in Montreal, June 1987.

FIG. 1 is a diagram showing the prior art with regard to target-centered two trunion arc systems. The transverse arc 1 is attached to trunions 5a and 5b and can rotate about the axis 7 by bearings in the trunions. Transverse carrier probe guide 2a or direction-determining guide which guides the probe track 3 to the target 4. The trunion axis 7 is oriented from left (L) to right (R) as shown relative to the patient's head. The head is fixed to some other object in the apparatus not shown, such as a head ring, and that head ring can be translated in x, y, z Cartesian space relative to the arc target 4 so that the arc target position can be translated to any physiologic point in the patient's head. The salient point here is that in the prior art the two trunion axis 7 remains fixed in angular orientation relative to the patient's head once the head ring attachment to the arc system has been secured to the patient's head.

To describe the situation in FIG. 1 in another way, the rotation of transverse arc 1 around its trunions 5a and 5b constitutes one angular movement or degree of freedom of probe track 3. The probe slide 2 moving on transverse arc 1 constitutes a second and orthogonal angular degree of freedom. The combination of these two rotations constitutes a two-dimensional angular degree of freedom which means that probe direction 3 covers a range of directions within the limits of the movements of the slide 2 on arc 1 and the rotation of transverse arc 1 about its trunions 5a and 5b. All of the radial directions 3 established in this way pass through the center of the circular arc 1. This means that if an anatomical target is translated to the position 4 at the arc center, then all radii will pass through that target. Thus if probe carrier 2a can be used to guide a surgical instrument or a beam of particles, then that instrument or particles will pass through the anatomical target if it is placed at the arc center. The range of radii achievable in such a situation can be likened to a surface area on the unit's sphere and an accompanying solid angle of approach in the terminology of solid geometry. The ideal stereotaxic system would maximize the solid angle or range of two-dimensional angle of approaches as described above. It is an objective of this patent to describe an augmentation of this range of approaches which has to do with the reorientatability of axis 7.

DESCRIPTION OF THE FIGURES

In FIG. 5a the trunions are positioned in the left-to-right orientation.

FIG. 6a is a view from above looking down on the patient's head with the apparatus attached. In FIG. 6a the trunions are in the position of left to right relative to the patient.

DESCRIPTION OF THE PRESENT INVENTION

Figure 1:
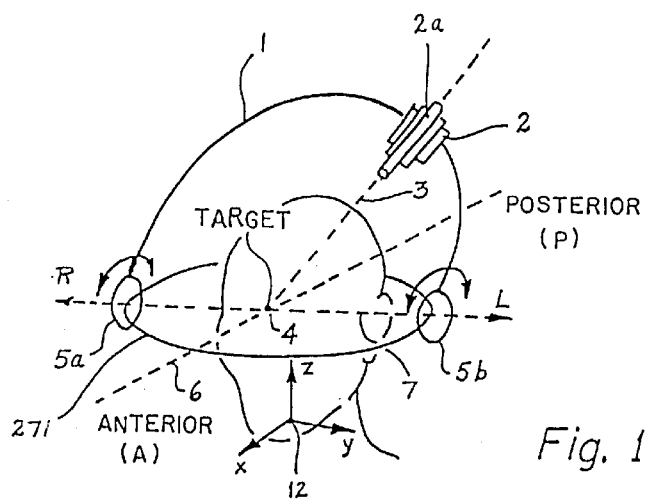
FIG. 1 is the prior art known in schematic form for a target-centered stereotaxic system with fixed trunion orientations. The line elements show schematically what would constitute mechanical pieces in the stereotaxic ; system.
Figure 2:
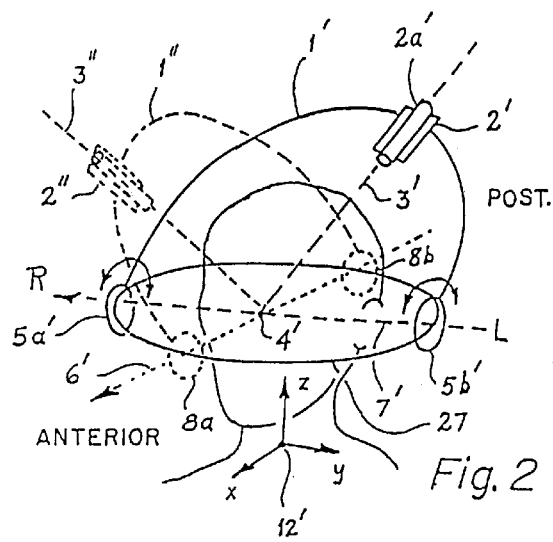
FIG. 2 is one embodiment of the present invention showing a target-centered stereotaxic arc in schematic form in which the transverse arc axis can be changed in its orientation relative to the patient's head or body-fixed means. In this case, the trunions are changed from the left-to-right orientation to the anterior-posterior orientation.

FIG. 2 shows a schematic diagram illustrating the present invention. Again, we have the patient's head with a body-fixed coordinate system x, y and z (12'). The target-centered arc, similar to that in FIG. 1, is also shown in the solid lines with trunion axis 7' running from left (L) to right (R), and transverse arc 1' rotating around the trunions with the probe carrier 2' and the probe guide 2a' again guiding the probe direction 3' to the target 4'. With rotations of the transverse arc 1' about axis 7', and slide movements of carrier transverse slide 2' on the transverse arc 1', almost any direction 3' can be achieved to target 4'. However, an exception is that the trunions 5a' and 5b' being on the left and right of the head, there is a limitation to how far carrier transverse slide 2' can slide down on arc 1' before bumping the trunions. This is one of the fundamental drawbacks of the previously designed target-centered arcs. Also shown in FIG. 2 is the relevant part of the present invention, namely the dashed lines showing the trunions 8A and 8B in an anterior-posterior position with associated rotation axis 6→ coming from front to back of the patient's head. In this situation, transverse arc 1" rotates around axis 6', and transverse carrier 2' slides on transverse arc 1' so that probe tract 3" can now achieve all directions including coming along the left-right direction (LR) in the horizontal plane 27. What is assumed here is that the head ring or body-fixed portion of the stereotaxic apparatus (not shown), that is attached to the body-fixed coordinate system 12', remains fixed relative to the patient and the entire arc system and trunions can be rotated 90° relative to the patient, so that the trunions 8a and 8b can be oriented 90° to trunion positions 5a' and 5b'. This degree of freedom of being able to move trunions has never been designed into a stereotaxic system until this invention.

Figure 3:
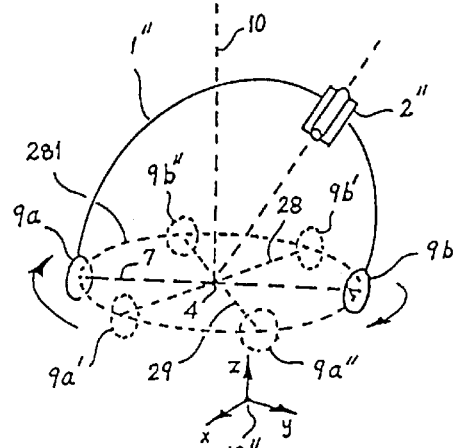
FIG. 3 is another schematic diagram illustrating the present invention in which the rotation axis of the transverse arc is shown in a multiplicity of orientations perpendicular to an axis which could be thought of as the long axis or axial direction relative to the patient's body.

FIG. 3 shows another configuration of the arc system in which the trunions 9a and 9b can be rotated in the plane indicated by the dashed circle >281 so that they can be oriented on an axis which is arbitrary in that plane 281. Notice for example the axes 28 and 29 which have been rotated at some arbitrary angle relative to axis 7" so that the trunions in 8a" and 9b'" or 9a' and 9b' are now at arbitrary positions. The corresponding transverse arc for these trunion positions is not shown in FIG. 3. In both FIG. 2 and FIG. 3 no specific means for translating target position 4' and 4" relative to the body-fixed coordinate origin 12' and 12" has been illustrated, but that will be shown later in FIG. 4 and beyond. We note that the design of FIG. 3 was reported by Cosman and Wells at the above-mentioned Montreal meeting in June 1987.

Figure 4:
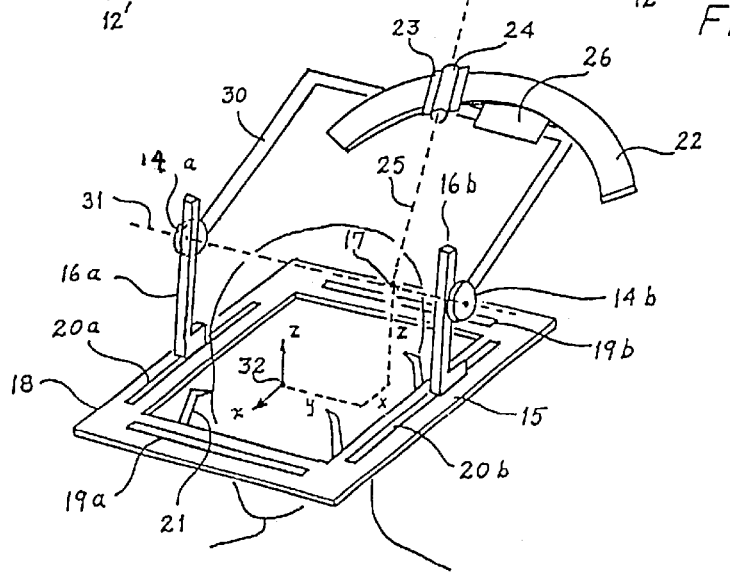
FIG. 4 is an embodiment of the present invention which shows the target-centered concept and also means for translating the position of the anatomical target to the center of the arc radii. In this embodiment, the trunions or bearings for the transverse arc axis can be oriented in the left-to-right position or in the anterior-posterior position. In the particular figure, the trunions are shown in a left-to-right position.
Figure 5A:
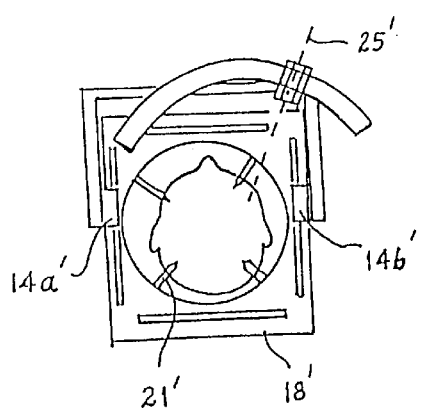
FIG. 5a is a schematic diagram of the device in FIG. 4 viewed from above looking down on the patient's head.
Figure 5B:
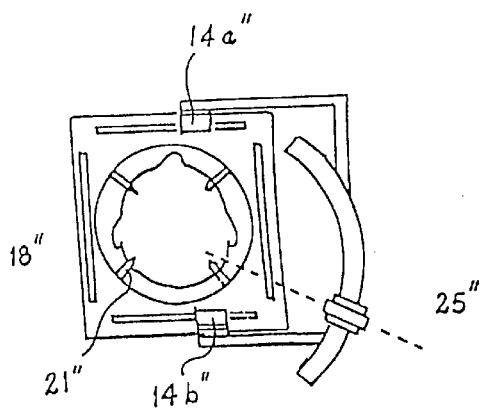
FIG. 5b is a schematic diagram of the same device as in FIG. 5a illustrating the present invention, but in this case the trunions of the transverse arc axis are located parallel to the anterior-posterior position relative to the patient.

FIG. 4 shows a more specific device design which indicates both the capability for angular reorientation of the trunions as described above, as well as the capability for translating the target position to the target center 17. Here we see a base platform 18 with slide grooves 20a and 20b located on the left and right side relative to the patient's head, as well as slide grooves 19a and 19b that are in the anterior and posterior position relative to the patient's head. The platform 18 is secured or fixed to the patient's skull by means of posts 21. The vertical posts 16a and 16b run in the grooves 20a and 20b along the anterior-posterior (A-P) or the x-axis direction. The trunions, 14a and 14b, run up and down in the vertical or z direction on the posts 16a and 16b, and in turn are attached to rectangular carrier 30 that can rotate about the trunion axis 31. On the upper portion of rectangular carrier 30 is a slide element 26 which is attached to the transverse arc 22, and this enables that the transverse arc can be slid in the lateral direction relative to the patient's head in this case or the y-axis direction. Again, the transverse arc 22 has a transverse slide which is 23 and probe carrier 24 to give probe guide direction 25 to a target on arc center 17. This illustrates then how the arc target 17, which is the center of the transverse arc 22, can be translated relative to the body-fixed origin 32. Thus, one can place the arc-centered target position at any anatomical position or anatomical target in the patient's head by such a movement. The entire assembly of trunions, vertical posts 16a and 16b can be taken up off the lateral slides 20a and 20b and placed in the anterior-posterior (A-P) located slides 19a and 19b so that the trunions will then be oriented in the front-to-back orientation as illustrated by the dashed trunions 8a and 8b in FIG. 2. This is diagrammatically shown in FIG. 5 which is a view down from above onto base 18 of FIG. 4 showing the different trunion positions. In FIG. 5a the trunions 14a' and 14b' are to the left and right of the patient's head respectively, the head being fixed by head posts 21' to the base plate 18'. The other features of the arc and rectangular attachment to the trunions are as discussed relative to FIG. 4. In FIG. 5b we see the same base plate 18" fixed to the head by post 21", but in this case the trunions 14a" and 14b" are positioned on the base plate 18", in the anterior and posterior orientations, respectively. The present invention, therefore, provides a means for changing the orientation of the trunions relative to the body-fixed means, in this case the base plate 18 of FIG. 4, after that body-fixed means has been attached to the patient's head. This will give maximum flexibility in the positioning and clearance of the arc movements after the patient has been prepared and set into the fixation means for the surgical procedure. As explained above, in all other stereotaxic systems to date the trunions have been fixed in a particular orientation such as left and right relative to the body-fixed means and do not provide for the kind of flexibility discussed relative to figures above. In FIGS. 4 and 5 the trunion orientations consist of two discrete orientations, namely left and right in FIGS. 4 and 5a and an anterior and posterior (front and back) in FIG. 5b relative to the patient's head or the body-fixed means, i.e. base plate 18, 18' and 18".

Figure 6A:
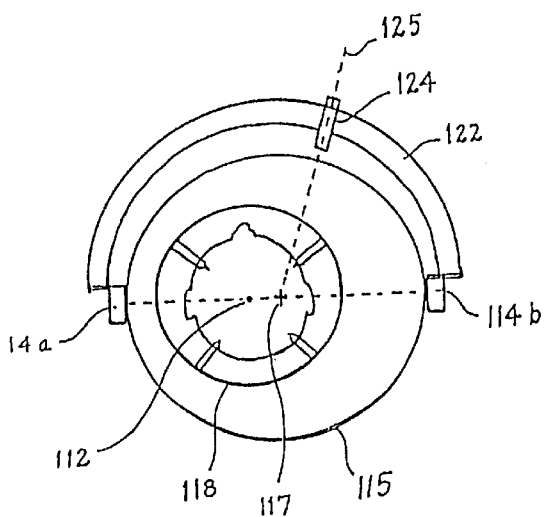
FIG. 6a is another schematic embodiment of the present invention in which the body-fixed head ring can be translated relative to a larger arc ring. The larger arc ring has a rotatable bearing which allows the transverse arc axis and its associated trunions to be rotated in an arbitrary angular direction about the long axis of the patient's body.
Figure 6B:
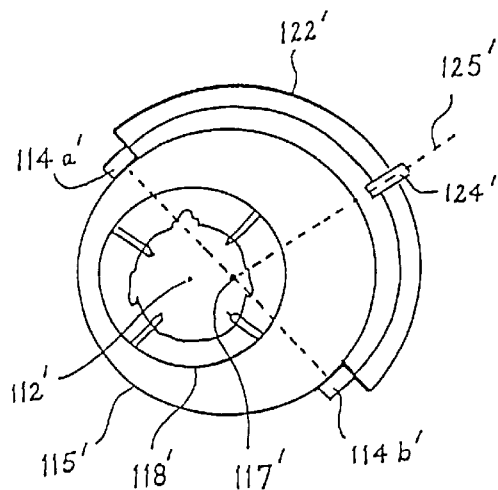
FIG. 6b shows the same schematic apparatus of FIG. 6a except that the trunions have been rotated to an arbitrary angle relative to the body-fixed head ring which shows the added reorientation degree of freedom described in this invention.

As indicated in FIG. 3, the orientation of the trunions can be at any angle relative to the anterior-posterior or left-to-right directions, not just the two discrete orientations as shown in FIG. 5. Indeed, the trunions could be attached to a structure which can rotate in any position relative to the patient fixation or body-fixed means. For example, in FIG. 6a and 6b, we see a circular head ring 118 and 118', respectively, with body-fixed origins of their coordinate systems 112 and 112', respectively. In FIG. 6a, the trunion-carrying ring 115, which can be angled in any orientation relative to fixation means 118, as are shown in this particular FIG. 6a with the trunions 114a and 114b in the left and right, or lateral orientation, relative to the head ring 118 and head. The arc 122 attaches to the trunions and the probe guide 124 can slide on arc 122 in any angular orientation to give a probe direction 125. In FIG. 6b, we see that the trunions have been rotated on ring 115' to a different angular orientation relative to the body fixation means 118'. There is an attachment of x, y and z slide movements coupling body fixation means 118 and the trunion carrying element 115, but this is not shown in FIG. 6. This can be done in any number of ways which are obvious, and one method has been described in the Montreal paper by Cosman and Wells.

In a similar fashion, and as an extension of the ideas shown in FIG. 6, the trunions could be rotated in a direction out of the plane of the paper; that is to say, the axis between the trunions could be rotated about a line within the plane of the paper and passing through the target isocenter 117 and 117'. It is also clear that many body fixation means, trunion carriers, and arc configurations can be devised by those skilled in the art. The transverse arcs shown in the figures are semicircles, but clearly they could be smaller or larger sectors of a circular geometry. The trunions could be replaced by simple shaft bearings, or orthogonal arc elements to accomplish similar movement of the arc about an axis. The transverse arc need only be supported on one end and these have only one bearing or trunion, not two as shown in the figures. Illustrated in the figures for body-fixed means are rings and platforms that can be anchored to the skull by appropriate posts and skull pins. Many other variations of the body fixation means could be devised that attach to the skull or any other part of the body in a variety of ways. These concepts could be extended to portions of the body other than the skull and could be used for passage not only of probes into the body but also alignment of collimators for external beam irradiation or any other applicators which require a stereotaxic quantitative guidance to a point in space. The latter application is becoming of increasing importance, and the present invention concept of a reorientatable arc axis which achieves a wider unobstructed range of approach to anatomical targets could have major importance. That anatomical point in space which would be at the center of the arc movements could be determined by various imaging modalities which are now in current use in medicine, such as x-ray, angiograms. CT or MRI scanners, and P.E.T. scanners.

It is also worth noting that the way one achieves the reorientation means of the arc system relative to the body-fixed means can take many forms. For example, as illustrated in FIG. 4, the reorientation means actually consists of grooves tracks that run in orthogonal directions on the base plate 18 which in turn is fixed to the patient. Thus, one can say that the reorientation means consists of structures on the body-fixed means itself. These structures accept the arc system as described above.

In contrast, as described by FIGS. 2, 3, and 6, it could be that the body-fixed means is a rigid head ring onto which an arc system can be attached. The arc system itself may have an azimuth or horizontal bearing structure that allows the transverse arc to be rotated about the patient's long axis or the axis of the head ring as illustrated graphically in FIG. 6a and 6b. The point here is that the reorientation means in these embodiments is completely embodied within the arc system. Thus the reorientation means may be partly in the body-fixation means, partly in the arc system, or partly combined in both of them. It also goes without saying that the arc system and the body-fixation means may be structurally integral, that is to say they are normally not separated. One could, for example, imagine the arc system to have head posts that can be fastened to the skull, and on the arc system is a means of changing the orientation of the trunions, as for example in a rotating bearing or slide mechanisms, etc.

A variance of the above described invention can be thought of by people skilled in the art, but we claim this to be within the general scope of this patent.

The claims we wish to secure by Letters Patent in the U.S. Patent Office are the following:

1. A target-centered stereotactic system for establishing a variable direction of access to a target in the living body comprising:
   a) a body-fixed means which includes an opening for receiving a portion of the living body and can be attached to the living body in a fixed orientation relative to said living body and defining an x, y and z axis;
   b) a transverse arc which is a portion of a circular arc segment and which is adapted to be rotatable connected relative to said body-fixed means;
   c) rotation means comprising two rotating bearings operatively connected to said transverse arc and also securable relative to said body-fixed means which allows said transverse arc to rotate about an arc axis that is parallel to the plane of said transverse arc;
   d) a slide means attached to and slidable along said transverse arc for determining a variable radial path relative to a circle having a diameter which lies along said arc axis with the center of said circle defining an anatomical target within the living body;
   e) reorientation means which allows variation of the angular orientation of said arc axis to said body-fixed means and thus said living body; and
   f) translation means adapted for translating said transverse arc relative to said body fixed means and thus said living body along each of said x, y and z axis, so as to move said anatomical target in said living body; whereby all of the variable radial paths defined by said slide means pass through said target, and whereby said variation of said arc axis orientation augments the range of said possible radial path to said anatomical target and whereby said slide means enables an approach of a surgical probe means to said anatomical target along a radial direction.

2. The apparatus of claim 1 wherein said body-fixed means has an axis of orientation which can be oriented approximately in the anterior-posterior (A-P) direction relative to said living body and wherein said reorientation means enables the arc axis to be established and fixed either parallel to said axis of orientation or perpendicular to said axis of orientations.

3. The apparatus of claim 2 wherein said body-fixed means has a plane of orientation and wherein said reorientation means enables the arc axis to be set at various angular positions about an axis that is perpendicular to said plane of orientation.

* * * * *